US012797369B2

(12) United States Patent
Kujala et al.

(10) Patent No.: US 12,797,369 B2
(45) Date of Patent: Nov. 17, 2026

(54) TASIPIMIDINE FORMULATIONS AND USE THEREOF

(71) Applicant: ORION CORPORATION, Espoo (FI)

(72) Inventors: Johanna Kujala, Espoo (FI); Jenni Lehtisalo, Espoo (FI); Jukka Salmia, Espoo (FI); Kai Sinervo, Espoo (FI)

(73) Assignee: ORION CORPORATION, Espoo (FI)

( * ) Notice: Subject to any disclaimer, the term of this patent is extended or adjusted under 35 U.S.C. 154(b) by 471 days.

(21) Appl. No.: 18/551,059

(22) PCT Filed: Mar. 18, 2022

(86) PCT No.: PCT/FI2022/050176

§ 371 (c)(1),
(2) Date: Sep. 18, 2023

(87) PCT Pub. No.: WO2022/195173

PCT Pub. Date: Sep. 22, 2022

(65) Prior Publication Data

US 2024/0165083 A1 May 23, 2024

(30) Foreign Application Priority Data

Mar. 19, 2021 (FI) ..................................... 20215311

(51) Int. Cl.

| | |
|---|---|
| ***A61K 31/4178*** | (2006.01) |
| ***A61K 9/00*** | (2006.01) |
| ***A61K 9/08*** | (2006.01) |
| ***A61K 47/12*** | (2006.01) |
| ***A61P 25/22*** | (2006.01) |

(52) U.S. Cl.

CPC ........ *A61K 31/4178* (2013.01); *A61K 9/0053* (2013.01); *A61K 9/0095* (2013.01); *A61K 9/08* (2013.01); *A61K 47/12* (2013.01); *A61P 25/22* (2018.01)

(58) Field of Classification Search

CPC ................................................ A61K 31/4178
USPC ........................................................ 514/402
See application file for complete search history.

(56) References Cited

U.S. PATENT DOCUMENTS

| | | | |
|---|---|---|---|
| 2019/0231749 | A1 | 8/2019 | Patel et al. |
| 2020/0308152 | A1 | 10/2020 | Laitinen et al. |

OTHER PUBLICATIONS

Korpivaara et al., "Tasipimidine, a novel orally active alpha-2 adrenoceptor agonist, alleviates canine acute anxiety associated with owner departure—A pilot study", BSAVA Congress 2021: Clinical Abstract Presentations, Jan. 1, 2021, p. 1, XP55929435 (Year: 2021).*

International Search Report of International Application No. PCT/FI2022/050176, mail date Sep. 2, 2022 (3 pages).

Mira Korpivaara et al., "Tasipimidine, a Novel Orally Active Alpha-2 Adrenoceptor Agonist, Alleviates Canine Acute Anxiety Associated With Owner Departure—A Pilot Study", *BSAVA Congress 2021: Clinical Abstract Presentations*, Jan. 2021 (1 page).

* cited by examiner

*Primary Examiner* — Jeffrey H Murray
*Assistant Examiner* — Rilla Marie Samsell
(74) *Attorney, Agent, or Firm* — Finnegan, Henderson, Farabow, Garrett & Dunner, LLP

(57) ABSTRACT

The present disclosure relates to a pharmaceutical composition in the form of an orally deliverable liquid composition comprising tasipimidine, or a pharmaceutically acceptable salt thereof, as an active ingredient and to the use thereof in the treatment and prevention of situational anxiety and fear in companion animals, such as dogs. The composition is stable at the pH range from about 2.0 to about 5.0 and it can be easily administered by the pet owners.

15 Claims, No Drawings

TASIPIMIDINE FORMULATIONS AND USE THEREOF

This is a National Stage Application under 35 U.S.C. § 371 of International Patent Application No. PCT/FI2022/050176, filed Mar. 18, 2022, which claims the benefit of priority of Finnish Patent Application No. 20215311, filed Mar. 19, 2021.

TECHNICAL FIELD

The present disclosure relates to a novel pharmaceutical composition in the form of an orally deliverable liquid pharmaceutical composition comprising tasipimidine, or a pharmaceutically acceptable salt thereof, as an active ingredient and to the use thereof in the treatment and prevention of situational anxiety and fear in companion animals, such as dogs.

BACKGROUND OF THE INVENTION

In the modern world many everyday situations put the adaptability of our companion dogs to the test and induce situational fear, anxiety and distress-based behavior in susceptible individuals. The prevalence of canine anxieties is not negligible. One online survey study of 4,114 dogs reported a prevalence of 44% for combined fear/anxiety with up to 85% of all behavioral complaints, combined. It is well known and acknowledged that situational anxieties and fears, especially those occurring frequently, reduce the quality of life of not only of the affected dogs but also of their caregivers. Failure to treat these anxieties can result in the disruption of the human-animal bond and the subsequent abandonment, relinquishment, reduced lifespan or, too often, even in euthanasia of the affected dog. Furthermore, as acute stress has been shown to enhance the memory of an event that is considered threatening, it is easy to understand that anxieties tend to be progressive, so that each negative experience will result in increased distress in subsequent anxiety inducing occasions. Sympathetic arousal is an early step in the response that causes distress. Common acute anxiety and fear inducing situations that provokes sympathetic arousal in dogs include events such as travel, noise, owner departure, and veterinary visits.

Fear of sudden loud noises is among the most common behavioral concerns for dog owners and it is often frequently inadequately and/or inefficiently treated. As the co-morbidity between noise anxiety and other anxieties has been documented, emphasis should be put on the early treatment of this condition in order to increase and ensure animal welfare.

Visiting a veterinary clinic has been demonstrated to be a stressful experience for the majority of dogs. Making veterinary visits less stressful for canine patients, their caregivers, and veterinary clinic personnel alike has been a point of focus during the recent years. Veterinary professionals are recommended to use more patient-centered handling approaches, and using pre-visit medications to facilitate the care of fractious individuals may be one step towards this goal.

Fear and anxiety related to travel is a common behavioral complaint in dogs. In one survey, up to 44% of dog owners described their dogs as having travel-related problems. Taking into account the fact that difficulties in traveling may also lead to lack of veterinary care, mitigation of travel anxiety is an important need that should be met.

Separation anxiety in dogs is a problematic behavior characterized by anxiety that occurs exclusively in the owner's absence or virtual absence. Typically, separation related behavior starts at the time when the owner prepares to leave, at the owner's departure or very shortly thereafter. Many dog owners have organized their lives so that the dogs are left alone rather occasionally, and thus might be more inclined to use pharmaceutical agents to help their dogs, if options for short-term use were available.

There is a widespread agreement on the behavioral signs representative of situational anxiety and fear. Situational fears and anxieties often present a clinical picture involving a number of non-specific signs of sympathetic arousal either alone or in combination such as: panting, restlessness/increased activity, trembling, salivation, vocalization, elimination, hyper-vigilance, hiding, avoidance, escape attempts or aggression when restrained. Behavioral signs that have been described in various situational anxiety and fear inducing situations in dogs are similar. Signs related to noise anxiety are non-specific and may include trembling, freezing, panting, social withdrawal, pacing, salivating, urinating, defecating, destruction, hiding/crouching (includes body lowering and tail tuck postures), and escape/running away behaviors. In one study 44% of dog owners described their dogs as having travel-related problems, and presenting similar signs. The most frequent behavioral signs exhibited were again vocalization, restlessness, panting, trembling, attention seeking, frequent swallowing, salivation and vomiting—all representing the classical signs of sympathetic arousal. The most frequently reported signs of owner departure induced distress are vocalization, destruction and elimination in the home, probably as these either disturb the dog's owner/neighbors or are also visible at the owner return. Less commonly recognized signs are restlessness/pacing, panting, salivation, inactivity, hiding, trembling and hypervigilance/orientation towards environment because a video recording is needed for their detection. When visiting the veterinary clinic, many dogs are anxious and/or fearful and exhibit avoidant and/or defensive behavior which also makes some of them very challenging to handle and causes a risk of injury to the dog itself and to the veterinary personnel alike. The signs of distress are similar as previously described for the other anxiety inducing situations. All of the aforementioned signs—although all not equally distressing to the owner—equally negatively influence the welfare of the affected dog. Conditions such as separation related distress, confinement distress and noise anxiety may be confused with each other due to the similar clinical signs, but accumulating evidence suggests that co-morbidities across anxieties exist and contribute to behavioral patterns of pathology.

The undesirable behaviors are significant in terms of the dog's welfare, and so relieving the distress of the affected dog should be a priority. There are currently no licensed medications for dogs that will relieve acute situational anxiety associated with sympathetic arousal. As behavioral problems are a major source of poor welfare and premature mortality in companion dogs, additional solutions are needed. From the animal welfare point of view as well as from the behavioral point of view (less progression to a more severe stage), it is of outmost importance that the treatment is started as early as possible and an option to of being able to try a temporary short-acting pharmacological solution might lower the hurdle.

Increased awareness of animal welfare and associated topics has created a need for safe and effective medication for treating situational anxieties and fears with a rapid onset of action and easy administration such that it can be given by the pet owners. This medication should not produce marked ataxia or excessive sedation. Being able to use a safe and effective medication as an initial pharmacological aid for this important welfare problem might motivate the owners to also seek long-term solutions to resolve this problem and may allow many dogs to learn to become less distressed.

Tasipimidine (2-(5-methoxyisochroman-1-yl)-4,5-dihydro-1H-imidazole) is a novel, orally active, selective alpha2A adrenoceptor agonist. Its high oral bioavailability and alpha2A selectivity differentiate it from dexmedetomidine, the currently approved and most specific alpha2 adrenoceptor agonist. WO 2014/060638 describes the use of dexmedetomidine oromucosal gel for alleviating the noise aversion in dogs and WO 2018/109272 describes the use of dexmedetomidine or medetomidine in treating separation anxiety in dogs. Tasipimidine and pharmaceutically acceptable salts thereof have been disclosed in WO 2013/150173. Tasipimidine exhibits agonistic activities on adrenergic alpha2 receptors, especially on alpha2A receptor, and can thus be used in the treatment of a disorder, condition or disease where an alpha2A agonist is indicated to be useful, for example, for use as a sedative or analgesic agent, and for use in the treatment of anxiety. Tasipimidine and salts thereof, particularly sulfate salt, may be prepared using the method described, for example, in WO 2019/106238.

SUMMARY OF THE INVENTION

It has now been found that tasipimidine, or a pharmaceutically acceptable salt thereof, particularly in the form of oral liquid pharmaceutical composition, is effective medicament for treating situational anxiety and fear in companion animals, such as dogs. The oral liquid pharmaceutical composition suitable for treating situational anxiety and fear, e.g. in dogs, comprises tasipimidine, or a pharmaceutically acceptable salt thereof, at a concentration of at least 0.04 mg/ml, preferably at least 0.20 mg/ml, more preferably at least 0.25 mg/ml. Tasipimidine sulfate drug substance as such has an excellent stability but addition of excipients impair its stability. However, it was found that the present composition is surprisingly stable at the pH range from about 2.0 to about 5.0. Thus, the composition of the present disclosure is particularly suitable for oral delivery in dogs. The composition has rapid onset of action in alleviating situational anxiety and fear in dogs. With the doses outlined in this application it does not produce marked ataxia or clinical sedation. Tasipimidine's high oral bioavailability allows precise and easy administration as oral solution, which is a convenient dosage form for pet owners. Ease of administration with a possibility to give further doses together with a longer duration of action and extended indication provides an advantage over the currently available medication and may cover somewhat prolonged acute situational anxiety and fear-inducing situations.

The foregoing as well as other feature and advantages of the present teachings will be more fully understood from the following description and claims.

DETAILED DESCRIPTION OF THE INVENTION

The present disclosure relates to a novel liquid pharmaceutical composition adapted for oral administration comprising a) tasipimidine, or a pharmaceutically acceptable salt thereof, as an active ingredient at a concentration of at least 0.04 mg/ml, preferably at least 0.20 mg/ml, more preferably at least 0.25 mg/ml;
b) a buffering agent;
c) a preservative; and
d) water:

wherein the pH of the composition is from about 2.0 to about 5.0, preferably from about 2.1 to 4.0, more preferably from about 2.5 to about 3.5, still more preferably from about 2.9 to about 3.1.

In one embodiment, tasipimidine, or a pharmaceutically acceptable salt thereof, particularly sulfate salt, is used as an active ingredient.

In one embodiment the present disclosure relates to above composition, which is a veterinary liquid pharmaceutical composition adapted for oral administration to a companion animal, particularly dog. The composition is, in particular, adapted to be given by the pet owners. The composition is particularly useful for the treatment or prevention of situational anxiety and fear in companion animals, such as dogs.

In one embodiment the situational anxiety is noise anxiety, veterinary visit anxiety, transportation anxiety, or separation anxiety.

The actual amount of tasipimidine, or a pharmaceutically acceptable salt thereof, to be administered may depend on numerous factors, such as the breed, age and weight of the companion animal to be treated. The amount of composition to be administered in suitably selected such as to provide sufficient situational anxiety and fear alleviating effect while not causing marked ataxia or clinical sedation in the treated animal. Accordingly, for the 20 treatment or prevention of situational anxiety and fear in companion animals, such as dogs, tasipimidine, or a pharmaceutically acceptable salt thereof, is administered generally in amount of about 0.01-0.06 mg/kg, preferably about 0.015-0.05 mg/kg, more preferably about 0.02-0.04 mg/kg, and typically about 0.025-0.035 mg/kg, for example about 0.03 mg/kg. The amount of tasipimidine, or a pharmaceutically acceptable salt thereof, is expressed throughout this document as a free base unless otherwise noted. The composition is suitably administered from about 0.5 to about 2 hours, more preferably from 1 to about 1.5 hours before the occurrence of possible situational anxiety or fear inducing event, such as noise, veterinary visit, transportation, or separation.

In one embodiment the present disclosure relates to a composition comprising tasipimidine, or a pharmaceutically acceptable salt thereof, as a sole active ingredient.

In one embodiment the present disclosure relates to the above composition which may comprise in addition to tasipimidine, or a pharmaceutically acceptable salt thereof, one or more other active ingredient(s), particularly those useful in the treatment or prevention of situational anxiety and fear in companion animals, particularly dogs.

The composition according to the present disclosure is preferably in the form of an aqueous solution adapted for oral administration to companion animals, particularly dogs. The concentration of tasipimidine, or a pharmaceutically acceptable salt thereof, should be high enough such that no impractically high amount of solution needs to be administered orally to companion animals, particularly dogs. Thus, the concentration of tasipimidine, or a pharmaceutically acceptable salt thereof, in the aqueous solution composition is at least 0.04 mg/ml, preferably at least 0.20 mg/ml, more preferably at least 0.25 mg/ml. For example, the concentration of tasipimidine, or a pharmaceutically acceptable salt thereof, is generally within the range from about 0.04 mg/ml to 3.0 mg/ml, preferably from about 0.1 mg/ml to 1.0 mg/ml, more preferably from about 0.2 mg/ml to 0.5 mg/ml, for example about 0.3 mg/ml.

It was found that stability of tasipimidine, or a pharmaceutically acceptable salt thereof, is improved in the composition having lower pH value. However, the formulations for oral administration should not have a pH below about 2 so that possible adverse effects like diarrhea, vomiting, tissue ulceration or necrosis and pain on administration could be avoided. The pH of the composition is suitably in the range from about 2.0 to about 5.0, preferably from about 2.1 to about 4.0, more preferably from about 2.5 to about 3.5, still more preferably from about 2.9 to about 3.1, for example about 3.0. At this pH range tasipimidine, or a pharmaceutically acceptable salt thereof, is found to be stable in the composition of the present disclosure. The pH of the composition can be adjusted to the desired range, for example, by using a pH adjusting agent(s). A pH adjusting agent may be a simple acid or base which does not have a pH buffering ability by itself, e.g. HCl or NaOH. Preferably, the solution is buffered. Suitable buffering agents include, but are not limited to, for example, lactic acid/lactate, citric acid/citrate, malic acid/malate, malonic acid/malonate, or phosphoric acid/phosphate buffers. Suitable buffer concentration is about 0.005-3 M, preferably about 0.005-1 M, more preferably about 0.01-1 M, even more preferably about 0.03-0.2 M, for example about 0.1 M. The buffers should be selected so that they do not have any negative effect on the palatability of the formulation to the companion animals, such as dogs. Particularly preferred buffering agent is 0.1 M citric acid/citrate buffer.

The composition suitably also comprise a preservative to inhibit microbial and/or fungal growth in the solution. The preservative is selected from agents that are physicochemically stable and active in the required pH range, do not have any negative effect on the palatability of the formulation and are compatible with the other components of the formulation. Examples of preservatives include, but are not limited to, benzoic acid and salts thereof such as sodium benzoate or potassium benzoate, sorbic acid and salts thereof such as potassium sorbate. Preservatives are commonly used in an amount of 0.01-1%, preferably 0.02-0.5%, for example 0.04-0.2%, per weight of the composition. It was found that benzoic acid salts such as sodium benzoate are particularly preferred preservatives. Benzoic acid salts such as sodium benzoate are preferably used in an amount of about 0.02-0.1% per weight of the composition.

The composition may further comprise one or more coloring agent(s). For example, a colored solution can be easily distinguished from saliva following the administration. If the liquid composition is discharged from the mouth of the animal the owner will be able to note the approximate loss of solution. The owner will also easily note any accidental dosing in case the solution comes into contact with his skin or if the solution is splashed onto the table or floor.

The composition may further comprise one or more flavoring agent(s). The flavoring agent is suitably selected such that it improves the palatability of the solution. In order to maintain the composition in the form of solution, the flavoring agent should also be water soluble, stable and compatible with the other components of the composition. Flavoring agents are generally used in amount of about 0.001-10%, preferably about 0.002-5%, more preferably about 0.002-1%, per weight of the composition.

In one embodiment the present disclosure relates to a veterinary liquid pharmaceutical composition adapted for oral administration to companion animals, particularly dogs, comprising a) tasipimidine, or a pharmaceutically acceptable salt thereof, as an active ingredient at a concentration of at least 0.04 mg/ml, preferably at least 0.2 mg/ml, more preferably at least 0.25 mg/ml;
b) citric acid/sodium citrate buffer
c) sodium benzoate; and
d) water;

wherein the pH of the composition is from about 2.0 to about 5.0, preferably from about 2.1 to about 4.0, more preferably from about 2.5 to about 3.5, still more preferably from about 2.9 to about 3.1.

In one embodiment the present disclosure relates to a veterinary liquid pharmaceutical composition adapted for oral administration to companion animals, particularly dogs, comprising a) about 0.004-0.3%, preferably about 0.01-0.1%, more preferably about 0.02-0.05%, per weight of the composition, of tasipimidine or a pharmaceutically acceptable salt thereof;
b) about 0.05-4.5%, preferably about 2.0-2.7%, more preferably about 2.2-2.3%, per weight of the composition, of a buffering agent;
c) about 0.01-1%, preferably about 0.02-0.5%, more preferably about 0.04-0.2%, per weight of the composition, of a preservative; and
d) about 96-98%, preferably about 97-97.9%, more preferably about 97.5-97.8%, per weight of the composition, of water;

wherein the pH of the composition is from about 2.0 to about 5.0, preferably from about 2.1 to about 4.0, more preferably from about 2.5 to about 3.5, still more preferably from about 2.9 to about 3.1.

In one embodiment the present disclosure relates to a veterinary liquid pharmaceutical composition adapted for oral administration to companion animals, particularly dogs, comprising a) about 0.004-0.3%, preferably about 0.01-0.1%, more preferably about 0.02-0.05%, per weight of the composition, of tasipimidine or a pharmaceutically acceptable salt thereof;
b) about 0.05-4.5%, preferably about 2.0-2.7%, more preferably 2.2-2.3%, per weight of the composition, of citric acid/citrate buffer;
c) about 0.01-1%, preferably about 0.02-0.5%, more preferably about 0.04-0.2% per weight of the composition, of a benzoic acid salt; and
d) about 96-98%, preferably about 97-97.9%, more preferably 97.5-97.8% per weight of the composition, of water;

wherein the pH of the composition is from about 2.0 to about 5.0, preferably from about 2.1 to about 4.0, more preferably from about 2.5 to about 3.5, still more preferably from about 2.9 to about 3.1.

The liquid pharmaceutical composition according to any of the embodiments above is an aqueous solution, i.e. composition where tasipimidine, or a pharmaceutically acceptable salt thereof, is in completely solubilized form.

In one embodiment the present disclosure relates to a composition comprising tasipimidine, or a pharmaceutically acceptable salt thereof, as an active ingredient for use in the treatment or prevention of situational anxiety and fear in companion animals, particularly dogs.

In one embodiment the present disclosure relates to the use of a composition comprising tasipimidine, or a pharmaceutically acceptable salt thereof, as an active ingredient in the manufacture of a medicament for the treatment or prevention of situational anxiety and fear in companion animals, particularly dogs.

In one embodiment the present disclosure relates to a composition comprising tasipimidine, or a pharmaceutically acceptable salt thereof, as an active ingredient in the manufacture of a medicament for the treatment or prevention of situational anxiety and fear in companion animals, particularly dogs.

In one embodiment the present disclosure relates to a method for the treatment or prevention of situational anxiety and fear in companion animals, particularly dogs, comprising administering to the subject in need thereof an effective amount of a composition comprising tasipimidine, or a pharmaceutically acceptable salt thereof, as an active ingredient.

In one embodiment the present disclosure relates to a medicinal kit comprising a) a liquid pharmaceutical composition adapted for oral administration comprising tasipimidine, or a pharmaceutically acceptable salt thereof, as an active ingredient, b) a package for containing said composition, and c) instructions for administering said composition to a companion animal, particularly dog, for the treatment or prevention of situational anxiety and fear. Preferably, said package is a glass bottle and it may further contain an applicator, such as a syringe, capable of dosing a suitable volumes of the composition.

Typically, the liquid pharmaceutical composition according to any of the embodiments above is administered orally 1 to 3 times a day (24 hrs), as needed, with at least 3 hours between doses.

The liquid pharmaceutical composition according to any of the embodiments above can be prepared e.g. by dissolving the active ingredient and excipients to water under stirring, followed by pH adjustment, if necessary.

Pharmaceutically acceptable salts of tasipimidine can be prepared by known methods. Suitable salts include acid addition salts formed, for example, with inorganic acids such as hydrochloric acid, hydrobromic acid, sulfuric acid, nitric acid, phosphoric acid and the like, and organic acids such as acetic acid, fumaric acid, propionic acid, glycolic acid, pyruvic acid, oxalic acid, napthalene-1,5-disulfonic acid, ethane-1,2-disulfonic acid and the like. Sulfate is the preferred salt.

The terms used herein have the meanings indicated below.

The term "situational anxiety and fear", as used herein, refers to a behavioral syndrome of companion animals, particularly dogs, characterized by signs of distress, fear, phobia or aggression when the animal is exposed to acute anxiety and fear inducing situations. Such signs include, but are not limited to, panting, restlessness, increased activity, attention seeking, trembling, shaking, salivating, frequent swallowing, vomiting, urinating, defecating, sweating paws, vocalization, barking, whining, crying, pacing, destruction, elimination, hypervigilance, freezing, hiding, crouching, avoidance, social withdrawal, inactivity, escape attempts, struggling or aggression when restrained.

The term "situational anxiety" as used herein, includes, but is not limited to, noise anxiety, veterinary visit anxiety, transportation anxiety, and separation anxiety.

The term "noise anxiety and fear", as used herein, refers to a behavioral syndrome of companion animals, particularly dogs, characterized by signs of distress, fear, phobia or aggression when the animal is exposed to a sudden loud noises, for example, gunshots, thunderstorms, fireworks or home alarms. Such signs include, but are not limited to, panting, trembling, salivating, urinating, defecating, destruction, freezing, hiding, crouching, social withdrawal, and escape attempts.

The term "veterinary visit anxiety and fear" as used herein, refers to a behavioral syndrome of companion animals, particularly dogs, characterized by signs of distress, fear, phobia or aggression when the animal visits a veterinarian or veterinary clinic or is examined or treated by veterinarian or veterinary clinic personnel alike. Such signs include, but are not limited to, panting, restlessness, trembling, vocalization, freezing, crouching, escape attempts, and struggling.

The term "transportation anxiety and fear" as used herein, refers to a behavioral syndrome of companion animals, particularly dogs, characterized by signs of distress, fear, phobia or aggression when the animal is moved to a transportation vehicle or is travelling in a transportation vehicle, for example, car, bus, train or airplane. Such signs include, but are not limited to panting, restlessness, attention seeking, trembling, salivating, frequent swallowing, vomiting, sweating paws, vocalization, destruction, freezing, hiding, and crouching.

The term "separation anxiety and fear" as used herein, refers to a behavioral syndrome of companion animals, particularly dogs, characterized by signs of distress, fear, phobia or aggression when the animal is left alone or is separated from the person or people to whom it is attached. Such signs include, but are not limited to vocalization, barking, pacing, destruction, elimination at home, panting, restlessness, trembling, salivating, urinating, defecating, hypervigilance, hiding, and inactivity and escape attempts.

The term "companion animal", as used herein, refers to an animal suitable for being kept as a pet by humans and including dogs and cats. The term "dog" include those dogs which are companion animals such as *Canis familiars*, working dogs and the like. The term dog is synonym with the term canine. The term "cat" includes those cats which are companion animals known as domestic cats or house cats, or *Felis domesticus*. The term cat is synonym with the term feline.

The term "tasipimidine", as used herein refers to 2-(5-methoxyisochroman-1-yl)-4,5-dihydro-1H-imidazole in free form and to pharmaceutically acceptable salts thereof, particularly a sulfate salt.

The term "preservative", as used herein, refers to a compound that inhibits microbial and/or fungal growth in the solution to which it is added.

The term "buffering agent" or "buffer", as used herein, refers to a compound or combination of compounds that when dissolved in water, resists changes to pH upon addition of acid or base, compared to water without the buffering agent added upon addition of the same amounts of the same acids and bases.

The term "liquid pharmaceutical composition", as used herein, refers to a pharmaceutical composition comprising a liquid carrier such as water, wherein the active ingredient, such as tasipimidine, or a pharmaceutically acceptable salt thereof, is at least partly, preferably completely, solubilized. Thus, in the preferred embodiment, "liquid pharmaceutical composition" is an aqueous solution.

The term "alleviating", as used herein, refers to reducing, inhibiting, preventing, suppressing or removing signs of situational fear and anxiety.

The term "clinical sedation", as used herein, means a state of relaxation characterized by reduced vigilance/alertness and depression of central nervous system functions without total loss of consciousness. Animals appear to be immobilized and sleeping (e.g. dogs are lying on the surface) and do not respond to normal stimulus. Clinical sedation in dogs in a study setting can be defined for instance by posture (lying±rising with great difficulty or unable to rise, unsteady gait), jaw tone (weakened or very weak), response to noise (no reaction) and ability to perform a particular procedure which requires sedation and restraint.

The present disclosure will be explained in more detailed by the following examples. The examples are meant for illustrating purposes only and do not limit the scope of the invention defined in the claims.

Example 1: Tasipimidine 0.3 mg/ml Oral Solution Having pH 3.0

| Ingredients | Quantity mg/ml |
|---|---|
| Tasipimidine sulfate | 0.30 (expressed as free base) |
| Trisodium citrate dihydrate | 5.29 |
| Citric acid monohydrate | 17.23 |
| Sodium benzoate | 0.50 |
| Brilliant Blue FCF | 0.01 |
| Tartrazine (E102) | 0.01 |
| Purified water | ad 1.0 ml |

The composition of example 1 was prepared by adding raw materials sequentially into the water and dissolved by mixing.

Following solutions containing 0.3 mg of tasipimidine as a free base and having pH 2-6.9 were prepared according to the method described above.

Example 2: Solution Having pH 2.0

| Ingredients | Quantity mg/ml |
|---|---|
| Tasipimidine sulfate | 0.30 (expressed as free base) |
| Sodium citrate dihydrate | — |
| Citric acid monohydrate | 21.01 |
| Sodium benzoate | — |
| Color FD&C blue no 1 | — |
| Color FD&C yellow no 5 | — |
| pH adjustment | — |
| Purified water | ad 1 ml |

Example 3: Solution Having pH 3.1

| Ingredients | Quantity mg/ml |
|---|---|
| Tasipimidine sulfate | 0.30 (expressed as free base) |
| Sodium citrate dihydrate | 5.29 |
| Citric acid monohydrate | 17.23 |
| Sodium benzoate | 0.50 |
| Color FD&C blue no 1 | 0.01 |
| Color FD&C yellow no 5 | 0.01 |
| pH adjustment | — |
| Purified water | ad 1 ml |

Example 4: Solution Having pH 3.6

| Ingredients | Quantity mg/ml |
|---|---|
| Tasipimidine sulfate | 0.30 (expressed as free base) |
| Sodium citrate dihydrate | 8.82 |
| Citric acid monohydrate | 14.71 |
| Sodium benzoate | 0.50 |
| Color FD&C blue no 1 | 0.01 |
| Color FD&C yellow no 5 | 0.01 |
| pH adjustment | — |
| Purified water | ad 1 ml |

Example 5: Solution Having pH 4.1

| Ingredients | Quantity mg/ml |
|---|---|
| Tasipimidine sulfate | 0.30 (expressed as free base) |
| Sodium citrate dihydrate | 12.06 |
| Citric acid monohydrate | 12.40 |
| Sodium benzoate | 0.50 |
| Color FD&C blue no 1 | 0.01 |
| Color FD&C yellow no 5 | 0.01 |
| pH adjustment | — |
| Purified water | ad 1 ml |

Example 6: Solution Having pH 4.9

| Ingredients | Quantity mg/ml |
|---|---|
| Tasipimidine sulfate | 0.30 (expressed as free base) |
| Sodium citrate dihydrate | 19.12 |
| Citric acid monohydrate | 7.35 |
| Sodium benzoate | — |
| Color FD&C blue no 1 | — |
| Color FD&C yellow no 5 | — |
| pH adjustment | — |
| Purified water | ad 1 ml |

Example 7: Solution Having pH 5.9

| Ingredients | Quantity mg/ml |
|---|---|
| Tasipimidine sulfate | 0.30 (expressed as free base) |
| Sodium citrate dihydrate | 26.03 |
| Citric acid monohydrate | 2.42 |
| Sodium benzoate | — |
| Color FD&C blue no 1 | — |
| Color FD&C yellow no 5 | — |
| pH adjustment | — |
| Purified water | ad 1 ml |

Example 8: Solution Having pH 6.9

| Ingredients | Quantity mg/ml |
|---|---|
| Tasipimidine sulfate | 0.30 (expressed as free base) |
| Sodium citrate dihydrate | 29.41 |
| Citric acid monohydrate | — |
| Sodium benzoate | — |

-continued

| Ingredients | Quantity mg/ml |
|---|---|
| Color FD&C blue no 1 | — |
| Color FD&C yellow no 5 | — |
| pH adjustment | 0.1M HCl q.s. to pH 7 |
| Purified water | ad 1 ml |

Experiment 1. Stability Study

An ASAP (Accelerated Stability Assessment Program) study to estimate the stability of tasipimidine sulfate in aqueous solution at 5° C. in pH range of about 2-7 was performed. The solutions of example 2 to 8 were stressed in temperatures 30, 40, 50, 60, 70 and 80° ° C. for 1-28 days. From the solutions, the main degradation product (N-(2-aminoethyl)-5-methoxy-3,4-dihydro-1H-2-benzopyran-1-carboxamide) was analyzed using HPLC and an estimation of the shelf life at 5° C. using the specification limit of 1.0% for degradation product was calculated. The calculation was performed using ASAP Prime software.

Stress conditions and degradation product results are presented in tables 1 to 7.

TABLE 1

Stress conditions and degradation product results of solution example 2 (pH 2.0).

| Stress temperature (° C.) | Stress time (days) | Degradation product (%) |
|---|---|---|
| 5 | ref | 0.00 |
| 30 | 14 | 0.19 |
| 40 | 14 | 0.60 |
| 50 | 7 | 1.00 |
| 50 | 14 | 1.94 |
| 60 | 2 | 0.87 |
| 60 | 4 | 1.77 |
| 70 | 2 | 2.38 |
| 70 | 4 | 4.60 |
| 80 | 1 | 2.81 |
| 80 | 2 | 5.72 |

TABLE 2

Stress conditions and degradation product results of solution example 3 (pH 3.1).

| Stress temperature (° C.) | Stress time (days) | Degradation product (%) |
|---|---|---|
| 5 | ref | 0.047 |
| 5 | ref | 0.045 |
| 30 | 28 | 0.047 |
| 40 | 14 | 0.045 |
| 40 | 28 | 0.499 |
| 50 | 7 | 0.843 |
| 50 | 14 | 1.637 |
| 60 | 3 | 0.826 |
| 60 | 7 | 1.765 |
| 70 | 2 | 1.530 |
| 70 | 7 | 4.095 |
| 80 | 1 | 2.396 |
| 80 | 2 | 9.189 |

TABLE 3

Stress conditions and degradation product results of solution example 4 (pH 3.6).

| Stress temperature (° C.) | Stress time (days) | Degradation product (%) |
|---|---|---|
| 5 | ref | 0.06 |
| 5 | ref | 0.06 |
| 30 | 28 | 0.62 |
| 40 | 14 | 1.05 |
| 40 | 28 | 2.03 |
| 50 | 7 | 1.05 |
| 50 | 14 | 2.35 |
| 60 | 3 | 1.95 |
| 60 | 7 | 5.00 |
| 70 | 2 | 3.02 |
| 70 | 7 | 10.72 |
| 80 | 1 | 3.70 |
| 80 | 2 | 9.69 |

TABLE 4

Stress conditions and degradation product results of solution example 5 (pH 4.1).

| Stress temperature (° C.) | Stress time (days) | Degradation product (%) |
|---|---|---|
| 5 | ref | 0.07 |
| 5 | ref | 0.07 |
| 30 | 28 | 0.80 |
| 40 | 14 | 1.36 |
| 40 | 28 | 2.60 |
| 50 | 7 | 1.46 |
| 50 | 14 | 2.96 |
| 60 | 3 | 2.82 |
| 60 | 7 | 6.93 |
| 70 | 2 | 3.92 |
| 70 | 7 | 14.71 |
| 80 | 1 | 5.34 |
| 80 | 2 | 13.59 |

TABLE 5

Stress conditions and degradation product results of solution example 6 (pH 4.9).

| Stress temperature (° C.) | Stress time (days) | Degradation product (%) |
|---|---|---|
| 5 | ref | 0.00 |
| 30 | 7 | 0.39 |
| 30 | 14 | 0.74 |
| 40 | 4 | 0.73 |
| 40 | 7 | 1.22 |
| 50 | 2 | 1.25 |
| 50 | 4 | 2.39 |
| 60 | 1 | 2.10 |
| 60 | 2 | 4.08 |
| 70 | 1 | 5.98 |
| 70 | 2 | 11.27 |

TABLE 6

Stress conditions and degradation product results of solution example 7 (pH 5.9).

| Stress temperature (° C.) | Stress time (days) | Degradation product (%) |
|---|---|---|
| 5 | ref | 0.09 |
| 30 | 7 | 0.96 |
| 30 | 14 | 1.81 |

TABLE 6-continued

Stress conditions and degradation product results of solution example 7 (pH 5.9).

| Stress temperature (° C.) | Stress time (days) | Degradation product (%) |
|---|---|---|
| 40 | 4 | 1.95 |
| 40 | 7 | 3.28 |
| 50 | 2 | 3.78 |
| 50 | 4 | 7.24 |
| 60 | 1 | 7.26 |
| 60 | 2 | 14.00 |
| 70 | 1 | 22.50 |
| 70 | 2 | 38.62 |

TABLE 7

Stress conditions and degradation product results of solution example 8 (pH 6.9).

| Stress temperature (° C.) | Stress time (days) | Degradation product (%) |
|---|---|---|
| 5 | ref | 0.29 |
| 30 | 7 | 4.28 |
| 30 | 14 | 7.93 |
| 40 | 4 | 9.87 |
| 40 | 7 | 16.03 |
| 50 | 2 | 20.06 |
| 50 | 4 | 31.63 |
| 60 | 1 | 35.14 |
| 60 | 2 | 41.89 |
| 70 | 1 | 49.93 |
| 70 | 2 | 49.03 |

TABLE 8

ASAP results. Median estimated shelf life and probability to pass 2 years shelf life for samples with pH from 2.0 to 6.9.

| Measured solution pH | 2.0 | 3.1 | 3.6 | 4.1 | 4.9 | 5.9 | 6.9 |
|---|---|---|---|---|---|---|---|
| Median estimated shelf life at 5° C. (years) | >3.00 | >3.00 | >3.00 | 2.57 | 2.25 | 1.47 | 0.17 |
| Probability to pass 2 years shelf life at 5° C. (%) | 100.0 | 100.0 | 99.9 | 87.0 | 60.6 | 28.3 | 0.7 |

The results show clearly that acidic condition protects tasipimidine from degradation. At pH 2.0-3.6, the estimated mean shelf life at 5° C. is >3 years when taking into account the 1.0% specification limit of the self life limiting degradation product.

Experiment 2. Clinical Studies in Dogs

Three randomized, double-blind, placebo-controlled, clinical field studies were conducted for evaluating the effectiveness and clinical safety of tasipimidine for the treatment of situational anxiety and fear-based behaviors in dogs triggered by events such as travel, noise, or owner departure. Across all three studies dogs were randomized to receive either 0.03 mg/kg of tasipimidine (n=131) or placebo (n=133) orally at home by the owner. Assessments were made using video (in the case of when left alone or car travel) or by the caretaker present during the fear inducing incident (in the case of noise anxiety). Both were assessed using a numerical rating scale with scores 1-5.

The first study was conducted in client-owned dogs with a history of acute anxiety and fear associated with noise due to fireworks. Dogs receive tasipimidine 30 μg/kg or placebo 1-3 times as needed with at least 3 hours between doses during New Year's Eve. The primary efficacy variable was the owner's assessment of the effect of study treatment on the dog's signs of acute anxiety and fear due to fireworks. The assessment was made once at least 2 hours after the last dose or at 1:00 A.M., whichever occurred later.

The second study was conducted in client-owned dogs suffering from separation anxiety. Dogs received tasipimidine 30 μg/kg or placebo 1-3 times a day as needed 5-7 days a week for 5 weeks. The primary efficacy variable was the owner's assessment of the effect of the study treatment on acute anxiety related to the owner's departure. Dog owners assessed the effect of the study treatment on their dog's signs of separation anxiety from video recordings after returning home. The owner also took into account the signs of the dog's behavior during the separation (e.g., destruction and elimination) that were not visible in the video recording.

The third study was conducted in client-owned dogs suffering from travel anxiety. Dogs received a single dose of tasipimidine 30 μg/kg or placebo approximately 1 hour before car travel. The primary efficacy variable was the external observer's assessment of signs of anxiety and fear from video recordings. The owner assessed the treatment effect based on the dog's behavior during the first 10 minutes of car travel.

A statistically significant treatment effect in favor of tasipimidine 30 μg/kg compared with placebo was seen in all three studies. Tasipimidine 30 μg/kg did not produce marked ataxia or clinical sedation.

A person skilled in the art will appreciate that the embodiments described herein can be modified without departing from the inventive concept. A person skilled in the art also understands that the present disclosure is not limited to the particular embodiments disclosed but is intended to also cover modifications of the embodiments that are within the scope of the present disclosure.

The invention claimed is:

1. A liquid pharmaceutical composition comprising:

a) tasipimidine, or a pharmaceutically acceptable salt thereof, as an active ingredient at a concentration of at least 0.04 mg/ml;

b) a buffering agent;

c) a preservative; and d) water;

wherein the pH of the composition is from about 2.0 to about 5.0; and wherein the liquid pharmaceutical composition is adapted for oral administration.

2. The composition according to claim 1, wherein the active ingredient is tasipimidine sulfate.

3. The composition according to claim 1, wherein the composition is a veterinary liquid pharmaceutical composition adapted for oral administration to a companion animal.

4. The composition according to claim 1, wherein the composition comprises about 0.004-0.3%, per weight of the composition, of tasipimidine, or a pharmaceutically acceptable salt thereof.

5. The composition according to claim 1, wherein the buffering agent is citric acid/sodium citrate buffer.

6. The composition according to claim 1, wherein the preservative is a benzoic acid salt.

7. The composition according to claim 6, wherein the preservative is sodium benzoate.

8. The composition according to claim 1, wherein the composition comprises:

a) tasipimidine, or a pharmaceutically acceptable salt thereof, as an active ingredient at a concentration of at least 0.04 mg/ml;

b) citric acid/sodium citrate buffer;

c) sodium benzoate; and d) water;

wherein the pH of the composition is from about 2.0 to about 5.0.

9. The composition according to claim 1, wherein the composition comprises:

a) 0.004-0.3%, per weight of the composition, of tasipimidine, or a pharmaceutically acceptable salt thereof;

b) 0.05-4.5%, per weight of the composition, of a buffering agent;

c) 0.01-1%, per weight of the composition, of a preservative; and d) 96-98%, per weight of the composition, of purified water;

wherein the pH of the composition is from about 2.0 to about 5.0.

10. The composition according to claim 9, wherein the composition comprises:

a) 0.01-0.1%, per weight of the composition, of tasipimidine or a pharmaceutically acceptable salt thereof;

b) 2.0-2.7%, per weight of the composition, of citric acid/citrate buffer;

c) 0.02-0.5%, per weight of the composition, of a benzoic acid salt; and d) 97-97.9%, per weight of the composition, of purified water;

wherein the pH of the composition is from about 2.0 to about 5.0.

11. The composition according to claim 1, wherein the buffering agent concentration is about 0.005-1 M.

12. The composition according to claim 1, wherein the concentration of tasipimidine, or a pharmaceutically acceptable salt thereof, is at least 0.25 mg/ml.

13. The composition according to claim 1, wherein the pH of the composition is from about 2.9 to 3.1.

14. The composition according claim 1, wherein the composition comprises about 0.02-0.05%, per weight of the composition, of tasipimidine, or a pharmaceutically acceptable salt thereof.

15. The composition according to claim 1, wherein the buffering agent concentration is about 0.1 M.

* * * * *